United States Patent
Han

(10) Patent No.: US 9,133,088 B1
(45) Date of Patent: Sep. 15, 2015

(54) PROCESS FOR HYDROXYLATING PHENOLIC SUBSTRATE

(71) Applicant: Yuan-zhang Han, New Hope, PA (US)

(72) Inventor: Yuan-zhang Han, New Hope, PA (US)

( * ) Notice: Subject to any disclaimer, the term of this patent is extended or adjusted under 35 U.S.C. 154(b) by 0 days.

(21) Appl. No.: 14/626,918

(22) Filed: Feb. 19, 2015

Related U.S. Application Data

(60) Provisional application No. 61/986,107, filed on Apr. 30, 2014, provisional application No. 62/038,966, filed on Aug. 19, 2014.

(51) Int. Cl.
*C07C 37/60* (2006.01)

(52) U.S. Cl.
CPC ..................... *C07C 37/60* (2013.01)

(58) Field of Classification Search
CPC ....................................... C07C 37/60
See application file for complete search history.

(56) References Cited

U.S. PATENT DOCUMENTS

| | | | |
|---|---|---|---|
| 3,849,502 A | 11/1974 | Bourdin et al. | |
| 4,013,727 A | 3/1977 | Umemura et al. | |
| 4,072,722 A | 2/1978 | Umemura et al. | |
| 4,078,006 A | 3/1978 | Umemura et al. | |
| 4,214,105 A | 7/1980 | Seifert et al. | |
| 4,223,165 A | 9/1980 | Jouffret et al. | |
| 5,331,103 A | 7/1994 | Costantini et al. | |
| 5,414,153 A | 5/1995 | Costantini et al. | |
| 5,434,317 A | 7/1995 | Costantini et al. | |
| 2014/0100392 A1* | 4/2014 | Lin et al. | 568/768 |

* cited by examiner

*Primary Examiner* — Brian J Davis

(57) ABSTRACT

The invention relates to a process for hydroxylating phenolic substrates such as phenols or phenol ethers. The process comprises reacting the phenolic substrate and hydrogen peroxide in the presence of a catalyst in a reaction mixture; and simultaneously removing water from the reaction mixture. The process improves the reaction rate, yield, and product selectivities.

15 Claims, 1 Drawing Sheet

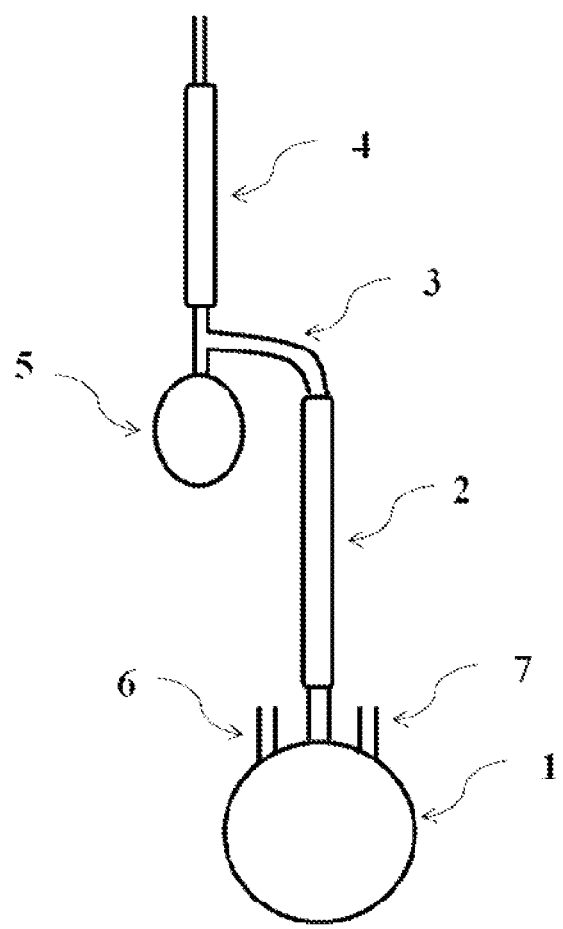

PROCESS FOR HYDROXYLATING PHENOLIC SUBSTRATE

This application claims the benefit under 35 U.S.C. §119 (e) of U.S. Provisional Application No. 61/986,107 filed on Apr. 30, 2014, and U.S. Provisional Application No. 62/038,966 filed on Aug. 19, 2014.

FIELD OF THE INVENTION

The present invention relates to a process for hydroxylating a phenolic substrate such as a phenol or a phenol ether with hydrogen peroxide.

DESCRIPTION OF THE PRIOR ART

Hydroxylation of phenol with hydrogen peroxide has been commercially practiced for several decades to produce hydroquinone (HQ) and pyrocatechol (CT). The hydroxylation reaction can be catalyzed by several types of catalysts, e.g., transition metals, strong acids, ketones, and titanium-containing zeolites. See, e.g., "Hydroquinone, Resorcinol, and Catechol," Kirk-Othmer Encyclopedia of Chemical Technology, on-line publication, Dec. 4, 2000.

There have been significant efforts in improving phenol hydroxylation reaction for producing hydroquinone and pyrocatechol, particularly in improving the reaction rate, the yield, and/or altering the ratio between hydroquinone and pyrocatechol. See, e.g., U.S. Pat. Nos. 3,849,502, 4,013,727, 4,072,722, 4,078,006, 4,214,105, 4,223,165, 5,331,103, 5,414,153, and 5,434,317.

U.S. Pat. No. 3,849,502 discloses a process for hydroxylating a phenol or phenol ether with hydrogen peroxide in the substantial absence of metal ions and in the presence of a catalytic amount of a strong acid having a pK value in water of below −0.1.

U.S. Pat. No. 4,013,727 discloses a process for hydroxylating a phenol ether with hydrogen peroxide in the presence of a ketone, or with a ketone peroxide, at a temperature of 20 to 250° C. in the presence of a catalyst selected from the group consisting of an activated clay, a boric acid or a boric acid derivative.

U.S. Pat. No. 4,072,722 discloses a process for preparing dihydric phenol derivatives by oxidizing monohydric phenol derivatives with a ketone peroxide in the presence or absence of sulfuric acid or a salt thereof or a sulfonic acid or a salt thereof.

U.S. Pat. No. 4,078,006 discloses a process for preparing dihydric phenol derivatives by oxidizing monohydric phenol derivatives with hydrogen peroxide in the presence of a ketone. The reaction is be promoted by sulfuric acid or a salt thereof or a sulfonic acid or a salt thereof.

U.S. Pat. No. 4,214,105 discloses a process for producing pyrocatechol and hydroquinone by hydroxylating phenol with hydrogen peroxide in the presence of a strong acid. At the start of the reaction, phenol is reacted with substantially anhydrous hydrogen peroxide in a non-aqueous solvent.

U.S. Pat. No. 4,223,165 discloses a process for hydroxylating phenols and phenol ethers with hydrogen peroxide in a reaction medium comprising trifluoromethanesulfonic acid at a temperature of about −40 and 10° C.

U.S. Pat. No. 5,331,103 discloses a process for hydroxylating a phenolic compound with hydrogen peroxide in the presence of a strong acid and a ketone and a polar aprotic organic solvent.

U.S. Pat. No. 5,434,317 discloses a process for hydroxylating a phenolic compound with hydrogen peroxide in the presence of a strong acid, an alkali metal salt thereof or an alkaline earth metal salt thereof, and a ketone. The selectivity to hydroquinone is increased by the use of benzophenone and its derivatives.

Industrially, there is a need for improvement in hydroxylating phenolic substrates such as phenols and phenol ethers.

First, the industry desires to use hydrogen peroxide with lower concentrations. Many of the patents discussed above teach using aqueous hydrogen peroxide having a concentration of at least 60 wt. %. Special precautions must be taken to handle concentrated hydrogen peroxide. Thus the industry desires to use about 30 wt. % aqueous hydrogen peroxide, which is more readily available, safer to use, and more economical.

Second, the industry desires to obtain higher yields in hydroxylating phenolic substrates such as phenols and phenol ethers so as to reduce the amount of waste generated by the manufacturing process.

Third, the industry desires to increase the rate of the reaction so as to reduce the amount of catalyst used and/or reduce the size and cost of the equipment for manufacturing products.

Forth, the industry desires to be able to alter the product selectivities based on the market needs. For example, hydroxylation of phenol produces hydroquinone and pyrocatechol. It is desirable to be able to control the ratio of hydroquinone to pyrocatechol.

In sum, there is a need to further improve the process for hydroxylating phenolic substrates such as phenols and phenol ethers

SUMMARY OF THE INVENTION

The invention is a process for hydroxylating a phenolic substrate, comprising: reacting the phenolic substrate and hydrogen peroxide in the presence of a catalyst selected from the group consisting of a strong acid, a ketone, and mixtures thereof, in a reaction mixture; and simultaneously removing water from the reaction mixture.

BRIEF DESCRIPTION OF THE DRAWINGS

FIG. 1 is a partial assembly of one apparatus that can be used to perform the process of the invention.

DETAILED DESCRIPTION OF THE INVENTION

The present invention relates to a process for hydroxylating a phenolic substrate, comprising: reacting the phenolic substrate and hydrogen peroxide in the presence of a catalyst selected from the group consisting of a strong acid, a ketone, and mixtures thereof, in a reaction mixture; and simultaneously removing water from the reaction mixture.

The process of the invention is suitable for phenolic substrates of general formula (I).

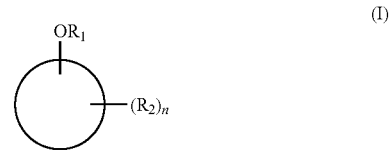

In formula (I), the circle symbolizes an aromatic core. $R_1$ represents a hydrogen atom or an alkyl, cycloalkyl, aryl or aralkyl group. $R_2$ represents a hydrogen atom or one or more identical or different substituents. The number of substituents on the aromatic core is represented by n, which is a number less than or equal to 15. In formula (I), the group –OR$_1$ is an ether group when R$_1$ is other than a hydrogen atom.

Examples of aromatic core include those shown in scheme II.

(II)

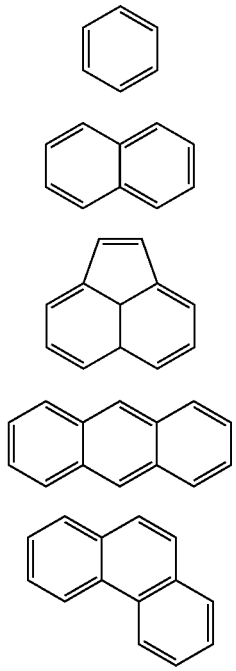

IIa

IIb

IIc

IId

IIe

The process is particularly suitable for phenolic substrates corresponding to formula (III):

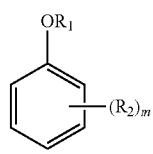

(III)

In formula (III), m is a number from 0 to 4 and preferably equals to 0, 1, or 2; R$_1$ represents a hydrogen atom or an alkyl, cycloalkyl, aryl or aralkyl group; R$_2$, which may be identical or different, represent an alkyl group, an alkoxy group, a hydroxyl group, a halogen atom, a haloalkyl, a perhaloalkyl group, or the like.

The process of the invention preferentially applies to substrates corresponding to formula (III) in which m is equal to 0 or 1; R$_1$ represents a hydrogen atom or an alkyl group containing from 1 to 4 carbon atoms; R$_2$ represents a hydrogen atom or an alkyl or alkoxy group containing from 1 to 4 carbon atoms.

In formulae (I) and (III), the term "alkyl" means a linear or branched C$_1$-C$_{15}$, preferably C$_1$-C$_{10}$, and more preferentially C$_1$-C$_4$ hydrocarbon-based chain. Examples of alkyl groups are methyl, ethyl, n-propyl, isopropyl, n-butyl, isobutyl, t-butyl, and the like.

The term "alkoxy" means a group "alkyl-O-" in which the term "alkyl" has the meaning given above. Preferred examples of alkoxy groups are methoxy and ethoxy groups.

The term "cycloalkyl" means a C$_3$-C$_8$ monocyclic hydrocarbon-based group, preferably a cyclopentyl or cyclohexyl group.

The term "aryl" means a monocyclic or polycyclic aromatic, preferably C$_6$-C$_{20}$ monocyclic or bicyclic group, preferably phenyl or naphthyl. When the group is polycyclic, i.e., when it comprises more than one cyclic nucleus, the cyclic nuclei may be fused in pairs or attached in pairs via a bonds. Examples of aryl groups are especially phenyl and naphthyl.

The term "aralkyl" means a linear or branched hydrocarbon-based group bearing an aromatic group; the aliphatic chain of the aralkyl group generally comprises 1 or 10 carbon atoms. Examples of aralkyl groups include benzyl, 1-phenylethyl, 2-phenylethyl, 1-phenylpropyl, 2-phenylpropyl, 3-phenylpropyl, and the like.

The term "haloalkyl group" means an alkyl group as defined previously in which one or more hydrogen atoms are replaced with a halogen atom, preferably a fluorine atom.

The term "perhaloalkyl group" means an alkyl group comprising from 1 to 10 carbon atoms and from 3 to 21 halogen atoms, preferably fluorine, and more particularly the trifluoromethyl group.

The term "halogen atom" defines fluorine, chlorine, and bromine.

Examples of preferred phenolic substrates that may be used in the process of the invention include phenol, anisole, o-cresol, m-cresol, p-cresol, 2-ethylphenol, 3-ethylphenol, 2-propylphenol, 2-sec-butylphenol, 2-tert-butylphenol, 3-tert-butylphenol, 4-tert-butylphenol, 2-methoxyphenol, 3-methoxyphenol, 4-methoxyphenol, 2-ethoxyphenol, methyl salicylate, 2-chlorophenol, 3-chlorophenol, 4-chlorophenol, 2,3-dimethylphenol, 2,5-dimethylphenol, 2,6-dimethylphenol, 3,5-dimethylphenol, 2,3-dichlorophenol, 2,5-dichlorophenol, 2,6-dichlorophenol, 3,5-dichlorophenol, 2,6-di-tert-butylphenol, 3,5-di-tert-butylphenol, 2,3,5-trimethylphenol, 2,3,6-trimethylphenol, 2,3,5-trichlorophenol, and 2,3,6-trichlorophenol. More preferred phenolic substrates includes phenol, o-cresol, m-cresol, p-cresol, anisole, phenetole, 2-methoxyphenol or 2-ethoxyphenol. One particularly preferred phenolic substrate is phenol, which can be used for producing hydroquinone and pyrocatechol.

The process of the invention uses hydrogen peroxide. Any source of hydrogen peroxide may be used. The hydrogen peroxide used may be in the form of an aqueous solution or a solution in an organic solvent. Since aqueous solutions of hydrogen peroxide are more readily available, they are preferably used. An aqueous hydrogen peroxide solution with H$_2$O$_2$ concentration of at least 20 wt. % and preferably from 20 to 90 wt. % is generally used. Conveniently, a commercially available aqueous hydrogen peroxide solution having a concentration of about 30 wt. % is used.

The amount of hydrogen peroxide used is not critical. Generally the molar ratio of H$_2$O$_2$ to the phenolic substrate is from 0.01:1 to 0.5:1, preferably from 0.02:1 to 0.3:1, more preferably from 0.03:1 to 0.2:1.

The process of the invention uses a catalyst selected from the group consisting of a strong acid, a ketone, and mixtures thereof. The process may use a strong acid as the catalyst. In the present invention, the term "strong acid" denotes an acid with a pKa in water of less than −0.1, preferably less than −1.0, more preferably less than −5.0. The pKa is defined as being the ionic dissociation constant of the acid/base pair when water is used as solvent. Among the acids corresponding to this definition, it is preferable to use those that are stable with respect to oxidation with hydrogen peroxide. Examples of suitable acid catalysts include sulfuric acid, perchloric acid, aliphatic or aromatic sulfonic acids (for example, methanesulfonic acid, ethanesulfonic acid, benzenesulfonic acid, toluenesulfonic acids, naphthalenesulfonic acids, benzenedisulfonic acids, naphthalenedisulfonic acids, trifluoromethanesulfonic acid, hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids, and hydroxynaphthalenedisulfonic acids), halosulfonic acids (for example, fluorosulfonic acid, chlorosulfonic acid), perhaloacetic acids (for example, trichloroacetic acid, trifluoroacetic acid), bis-trifluoromethanesulfonimide, sulfonic acidic resins, and the like. More preferred acid catalysts include sulfuric acid, perchloric acid, methanesulfonic acid, ethanesulfonic acid, benzenesulfonic acid, toluenesulfonic acids, naphthalenesulfonic acids, trifluoromethanesulfonic acid, fluorosulfonic acid, chlorosulfonic acid, trichloroacetic acid, trifluoroacetic acid, bis-trifluoromethanesulfonimide, sulfonic acidic resins, and the like. Most preferred strong acid catalysts include sulfuric acid, perchloric acid, methanesulfonic acid, trifluoromethanesulfonic acid, fluorosulfonic acid, chlorosulfonic acid, trichloroacetic acid, trifluoroacetic acid, and the like. Particularly preferred acid catalysts include perchloric acid and trifluoromethanesulfonic acid.

The amount of the strong acid used in the process of the invention is not critical. Generally the molar ratio of the acid catalyst to the phenolic substrate is from 0.00001:1 to 0.05:1, preferably 0.0001:1 to 0.01:1, more preferably 0.0002:1 to 0.005:1.

The process may use a ketone as the catalyst. The ketone is represented by formula (IV):

In formula (IV), $R_3$ and $R_4$ are any hydrocarbon-based groups. $R_3$ and $R_4$ may be linear or branched alkyl groups, linear or branched alkenyl groups, cycloalkyl or cycloalkenyl groups, monocyclic or polycyclic aryl groups, and the like. Generally, $R_3$ and $R_4$ contain from 1 to 30 carbon atoms. $R_3$ and $R_4$ may form a divalent group. $R_3$ and $R_4$ may have substituent such as hydroxy, ketone, ester, ether, carboxylic acid, halogen, and the like.

Examples of suitable ketones include acetone, methylethylketone, 2-pentanone, 3-pentanone, 3-methyl-2-butanone, 2-hexanone, 3-hexanone, 3-methyl-2-pentanone, 4-methyl-2-pentanone, 3,3-dimethyl-2-butanone, 2-heptanone, 3-heptanone, 2,4-dimethyl-3-pentanone, 2-octanone, 6-methyl-2-heptanone, 2-nonanone, 2,6-dimethyl-4-heptanone, 2,2,4,4-tetramethyl-3-heptanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, cyclopentanone, cyclohexanone, 2-ethyl-1-cyclopentanone, 2-methyl-1-cyclohexanone, cyclododecanone, 2,3-butanedione, 2,4-pentanedione, 2,5-hexanedione, benzophenone, 2-methylbenzophenone, 2,4-dimethylbenzophenone, 4,4'-dimethylbenzophenone, 2,2'-dimethylbenzophenone, 4,4'-dimethoxybenzophenone, 4-hydroxybenzophenone, 4,4'-dihydroxy benzophenone, 4-benzoylbiphenyl, acetophenone, ethyl phenyl ketone, n-propanyl phenyl ketone, and the like.

A ketone precursor may be used. A ketone precursor is a compound that can be converted to a ketone under the process conditions. For example, a secondary alcohol may be oxidized to the corresponding ketone by hydrogen peroxide, thus a secondary alcohol is a suitable ketone precursor. Suitable secondary alcohols include 2-propanol, 2-butanol, 2-pentanol, 3-methyl-2-butanol, 2-hexanol, 3-hexanol, 3-methyl-2-pentanol, 4-methyl-2-pentanol, 3,3-dimethyl-2-butanol, 2-heptanol, 3-heptanol, 2,4-dimethyl-3-pentanol, 2-octanol, 6-methyl-2-heptanol, 2-nonanol, 2,6-dimethyl-4-heptanol, 2,2,4,4-tetramethyl-3-pentanol, 3-decanol, 6-undecanol, 2-tridecanol, 7-tridecanol, 2-tetradecanol, 2-pentadecanol, 2-hexadecanol, 2-heptadecanol, 2-octadecanol, 3-octadecanol, 4-nonadecanol, 3-buten-2-ol, 3-penten-2-ol, 5-hexen-2-ol, 4-methyl-3-penten-2-ol, 6-methyl-5-hepten-2-ol, 5-octen-2-ol, 7-nonadecen-2-ol, 1-chloro-2-butanol, 1-chloro-3-heptanol, 3-hydroxy-2-butanol, 1-bromo-3-heptanol, 1-hydroxy-2-propanol, 4-amino-4-methyl-2-pentanol, 1-phenylethanol, diphenylmethanol, 1-phenyl-2-propanol, 1-phenyl-1-propanol, 1-phenyl-1-butanol, 1-phenyl-3-butanol, 1-phenyl-3-pentanol, 1,3-diphenyl-2-propanol, 2,3-butanediol, 2,4-pentanediol, 2,5-hexanediol, cyclopentanol, cyclohexanol, 2-ethyl-1-cyclopentanol, 2-methyl-1-cyclohexanol, etc.

Another group of suitable ketone precursors are acetals or hemiacetals. An acetal is represented by formula (V). A hemiacetal is represented by formula (VI).

In formula (V) and (VI), $R_5$, $R_6$, $R_7$, and $R_8$ are independently any hydrocarbon-based groups. $R_5$, $R_6$, $R_7$, and $R_8$ may be linear or branched alkyl groups, linear or branched alkenyl groups, cycloalkyl or cycloalkenyl groups, monocyclic or polycyclic aryl groups, and the like. Generally, $R_5$, $R_6$, $R_7$, and $R_8$ contain from 1 to 30 carbon atoms. $R_5$ and $R_6$ may form a divalent group. $R_7$ and $R_8$ may form a divalent group. $R_5$, $R_6$, $R_7$, and $R_8$ may have substituent such as hydroxy, ketone, ester, ether, carboxylic acid, halogen, and the like.

The amount of ketone present in the process is not critical. Generally the molar ratio of the ketone to the phenolic substrate may be from 0.0001:1 to 0.2:1, preferably from 0.001:1 to 0.1:1, more preferably from 0.005:1 to 0.05:1.

When the process uses a ketone as a catalyst, it may be performed in the presence of a promoter. A promoter helps to accelerate the reaction or improve the selectivity to a desired product. A sulfur-containing substance may be used as a promoter. One group of suitable sulfur-containing promoters include sulfates (salts of sulfuric acid), for example, ammonium sulfate, lithium bisulfate, sodium sulfate, sodium bisulfate, magnesium sulfate, aluminum sulfate, potassium sulfate, potassium bisulfate, cerium sulfate, hydroxylamine sulfate, dibutylamine sulfate, aniline sulfate, pyridine sulfate, piperidine sulfate, etc.

A chemical compound that may be converted to a sulfate under the process conditions may be used as a promoter precursor. For example, sulfites, bisulfites, sulfur dioxide may be oxidized to sulfates under the process conditions. An ester of sulfuric acid may also be converted to sulfuric acid or sulfates under the process conditions.

Another group of suitable sulfur-containing promoters include sulfonates (salts of sulfonic acids), for example, metal salts, ammonium salts, and organic base salts of methanesulfonic acid, ethanesulfonic acid, benzenesulfonic acid, p-toluenesulfonic acid, p-phenolsulfonic acid, p-aminosulfonic acid, naphthalene-α-sulfonic acid, and sulfonic acid type resins.

A chemical compound that may be converted to a sulfonate may be used as a promoter precursor. For example, an alkyl and aryl thiol may be oxidized to a sulfonic acid or a sulfonate under the process conditions. An ester of a sulfonic acid may also be converted to a sulfonic acid or a sulfonate under the process conditions.

The amount of the promoter present in the process is not critical. Generally the molar ratio of the promoter to the phenolic substrate may be from 0.00001:1 to 0.05:1, preferably from 0.0001:1 to 0.01:1, more preferably from 0.0002:1 to 0.005:1.

The process may use a combination of a strong acid described above and a ketone described above as the catalyst.

The process may use a complexing agent for metal ions that may be present in the reaction mixture since some metal ions, particularly transition metal ions such as iron, nickel, copper, chromium, cobalt, manganese and vanadium ions are harmful to the process. The transition metal ions may have been introduced by the phenolic substrate, hydrogen peroxide reagent, or others. To inhibit the action of these metal ions, it is desirable to perform the reaction in the presence of one or more complexing agents that are stable with respect to hydrogen peroxide and which form complexes under the process conditions. Examples of complexing agents include orthophosphoric acid, meta-phosphoric acid, pyrophosphoric acid, polyphosphoric acids, phosphonic acids such as (1-hydroxyethylidene)diphosphonic acid, phosphonic acid, ethylphosphonic acid, and phenylphosphonic acid. Esters of the above mentioned acids such as monoalkyl or dialkyl, monocycloalkyl or dicycloalkyl, or monoalkylaryl or dialkylaryl orthophosphates, for example, ethyl or diethyl phosphate, hexyl phosphate, cyclohexyl phosphate or benzyl phosphate may also be used as complexing agent in the process. One particularly preferred complexing agent is pyrophosphoric acid.

The amount of the complexing agent used depends on the metal ion content in the reaction mixture. The molar ratio of the complexing agent to the phenolic substrate is generally from 0.00001:1 to 0.1:1, preferably from 0.00005:1 to 0.05:1, more preferably from 0.0001:1 to 0.01:1.

The process is generally performed at a temperature of from 30 to 180° C., preferably from 40 to 150° C., more preferably from 50 to 130° C.

The process comprises: reacting the phenolic substrate and hydrogen peroxide in the presence of a catalyst in a reaction mixture; and simultaneously removing water from the reaction mixture. Water may have been introduced to the reaction mixture by the phenolic substrate or the hydrogen peroxide reagent. Water is also a byproduct from the hydroxylation of the phenolic substrate by hydrogen peroxide.

The manner in which the water is removed from the reaction mixture is not critical. For example, water may be removed from the reaction mixture by distillation from the reaction mixture during the reaction, preferably at a sub-atmospheric pressure. The distillation may be a simple one-stage distillation. Alternatively, the distillation may be carried out with a distillation column with bubble cap trays, valve trays, sieve trays, or a packed column containing random packing or ordered packing. The distillation column preferably has from 2 to 30 theoretical plates, more preferably from 3 to 20 theoretical plates. Preferably the distillation is carried out at a temperature of from 50 to 120° C., more preferably from 60 to 110° C., and preferably at a pressure of from 1 to 500 mmHg, more preferably from 3 to 100 mmHg.

While water is being removed from the reaction mixture, a portion of the phenolic substrate, the ketone (if used), and hydrogen peroxide may also be removed along with water from the reaction mixture. The removed mixture may be further processed or purified to recover the phenolic substrate, the ketone, and the hydrogen peroxide, which may be re-used in the process.

Other methods of removing water from the reaction mixture may be used. For example, a solvent may be added to the reaction mixture. In this case, water may be distilled together with the solvent. Suitable solvents include aromatic hydrocarbons, esters, nitriles, halogenated hydrocarbons, amide, and the like. Examples of suitable solvents include toluene, xylene, ethyl acetate, chlorobenzene, acetonitrile, nitrobenzene, and the like.

Yet another method of removing water from the reaction mixture is gas stripping. A gas may be sparged to the reaction mixture to carry water away from the reaction mixture. Suitable gas may include air, nitrogen, other inert gases, methane, and the like.

The water may be removed from the reaction mixture continuously, or at intervals.

The water concentration in the reaction mixture of the process is generally controlled at less than 1.5 wt. %, preferably less than 1.0 wt. %, more preferably less than 0.50 wt. %, most preferably less than 0.10 wt. %.

There may be many ways to carry out the process. The process may be performed in a batch mode, a semi-continuous mode, or a continuous mode.

EXAMPLE 1

A partial assembly of an apparatus is shown in FIG. 1. A three-neck 250-mL round-bottom flask 1 (also called "reactor") is equipped with a distillation column 2 (25 cm in length, 2.5 cm internal diameter). A glass thermo well (not shown) is fitted through the neck 6 of flask 1, extending inside the flask. A thermal couple is fitted in the thermo well to measure the temperature of the reaction mixture. A magnetic stirring bar (not shown) is used in the flask. The distillation column 2 is packed with random packing (5 theoretical plates) and wrapped with glass wool to prevent heat loss. A distillation head 3 is installed on the top of the distillation column 2. A condenser 4 and a collection flask 5 are installed on the distillation head 3. The collection flask is chilled at 2° C. with a coolant during the reaction. The top of condenser 4 is fitted to a pressure measuring device and a vacuum pump (not shown). A coolant at 2° C. is circulated to the condenser during the reaction. Aqueous hydrogen peroxide solution is added by a pump through neck 7 of the reactor. A hot water bath provides heat to the flask.

Phenol (153.85 g, 1.63 mole), 70 wt. % aqueous perchloric acid ($HClO_4$) solution (0.28 g, 0.0020 mole), and 90 wt. % pyrophosphoric acid ($H_4P_2O_7$) solid (0.14 g, 0.00071 mole) was charged to the reactor. The mixture was heated to 72° C. with a water bath at 75° C. while the reactor content was mixed by a stirring bar. The pressure is controlled at 27 mmHg with a vacuum pump. A 30 wt. % aqueous $H_2O_2$ solution (11.61 g, 0.102 mole) was added to the flask during a period of 52 min at a constant addition rate. The temperature in the reactor was maintained at 72° C. The pressure in the reactor was maintained at 27 mmHg. Certain quantity of liquid accumulated in the collection flask. When the addition of $H_2O_2$ solution stopped, the temperature in the reactor rose to 75° C. The reaction lasted for another 8 min after the addition of $H_2O_2$ solution.

The liquid in the collection flask and any liquid remaining in the random packing in the distillation column were combined and referred to as "distilled mixture." The distilled mixture and the reactor content were weighed and analyzed by HPLC. The results are shown in Table 1. The distilled mixture contains water, phenol, and $H_2O_2$. A total of 3.33 g $H_2O_2$ (pure form) was consumed. The $H_2O_2$ conversion in the reactor was >99.8%. The selectivity to hydroquinone (HQ) relative to $H_2O_2$ converted was 38.2%. The selectivity to pyrocatechol (CT) relative to $H_2O_2$ converted was 47.5%. The total selectivity to hydroquinone and pyrocatechol (CT) relative to $H_2O_2$ converted was 85.7%.

EXAMPLES 2-6

The procedure of Example 1 was repeated. Details are shown in Table 1.

with a water bath while the reactor content was mixed by a stirring bar. A 30 wt. % aqueous $H_2O_2$ solution (9.58 g, 0.085 mole) was added to the flask through the addition funnel during a period of 2 min. The temperature in the reactor was maintained at 75° C. Samples taken at 70 min, 120 min, and 180 min after the addition of $H_2O_2$ were analyzed by HPLC. The results are shown in Table 2.

TABLE 2

| Example | C. 7-1 | C. 7-2 | C. 7-3 |
| --- | --- | --- | --- |
| Feed | | | |
| Phenol (g) | 153.19 | 153.19 | 153.19 |
| 30% $H_2O_2$ (g) | 9.58 | 9.58 | 9.58 |
| 70% $HClO_4$ (g) | 0.14 | 0.14 | 0.14 |
| 90% $H_4P_2O_7$ (g) | 0.14 | 0.14 | 0.14 |
| Reactor Temp. (° C.) | 75 | 75 | 75 |
| Reaction Time (min) | 70 | 120 | 180 |
| $H_2O_2$ Conversion (%) | 48.1 | 64.0 | 80.4 |
| Selectivity to HQ (%) | 29.6 | 30.0 | 28.6 |
| Selectivity to CT (%) | 42.0 | 43.0 | 42.5 |

TABLE 1

| | Example | | | | | |
| --- | --- | --- | --- | --- | --- | --- |
| | 1 | 2 | 3 | 4 | 5 | 6 |
| Feed | | | | | | |
| Phenol (g) | 153.85 | 153.76 | 153.95 | 153.53 | 153.32 | 153.84 |
| 30% $H_2O_2$ (g) | 11.61 | 11.42 | 11.78 | 11.22 | 9.86 | 9.85 |
| 70% $HClO_4$ (g) | 0.28 | 0.28 | 0.28 | 0.14 | 0.28 | 0.14 |
| 90% $H_4P_2O_7$ (g) | 0.14 | 0.14 | 0.14 | 0.14 | 0.14 | 0.14 |
| Pressure (mmHg) | 27 | 27 | 27 | 27 | 27 | 27 |
| Bath Temp. (° C). | 75 | 70 | 80 | 75 | 75 | 75 |
| Reactor Temp. during $H_2O_2$ Addition (° C.) | 72 | 67 | 77 | 72 | 72 | 72 |
| $H_2O_2$ Addition Time (min) | 52 | 52 | 52 | 52 | 44 | 81 |
| Reactor Temp. After $H_2O_2$ Addition (° C.) | 75 | 70 | 80 | 75 | 75 | 75 |
| Time After $H_2O_2$ Addition (min) | 8 | 8 | 8 | 8 | 10 | 4 |
| Distilled Mixture Collected | | | | | | |
| Phenol (g) | 8.35 | 4.54 | 9.62 | 6.53 | 8.39 | 6.21 |
| Pure $H_2O_2$ (g) | 0.15 | 0.18 | 0.090 | 0.38 | 0.087 | 0.096 |
| Reactor Content Wt. (g) | 145.49 | 151.41 | 145.77 | 147.66 | 146.43 | 149.05 |
| Pure $H_2O_2$ (g) | <0.01 | <0.01 | <0.01 | <0.01 | <0.01 | <0.01 |
| Hydroquinone (g) | 4.02 | 3.90 | 4.10 | 3.70 | 3.55 | 3.52 |
| Pyrocatechol (g) 4.99 | 4.94 | 5.16 | 4.56 | 4.51 | 4.49 | |
| Converted $H_2O_2$ (g) | 3.33 | 3.25 | 3.44 | 2.99 | 2.87 | 2.86 |
| (Converted $H_2O_2$)/(Phenol in Feed) (mol/mol) | 0.060 | 0.058 | 0.062 | 0.054 | 0.052 | 0.051 |
| $H_2O_2$ Conversion in Reactor (%) | >99.8 | >99.8 | >99.8 | >99.8 | >99.8 | >99.8 |
| Selectivity to HQ (%) | 38.2 | 37.2 | 36.9 | 38.2 | 38.2 | 38.0 |
| Selectivity to CT (%) | 47.5 | 47.1 | 46.3 | 47.1 | 48.5 | 48.5 |
| Selectivity to (HQ + CT) (%) | 85.7 | 84.3 | 83.2 | 85.3 | 86.7 | 86.5 |
| CT/HQ (mole/mole) | 1.24 | 1.27 | 1.26 | 1.23 | 1.27 | 1.28 |

COMPARATIVE EXAMPLE 7

A three-neck 250-mL round-bottom flask (also referred to as "reactor") is equipped with a condenser, a glass thermo well, an addition funnel, and a magnetic stirring bar. A thermal couple is fitted in the thermo well to measure the temperature of the reaction mixture. A hot water bath provides heat to the flask.

Phenol (153.19 g, 1.63 mole), 70 wt. % aqueous perchloric acid ($HClO_4$) solution (0.14 g, 0.00098 mole), and 90 wt. % pyrophosphoric acid ($H_4P_2O_7$) solid (0.14 g, 0.00071 mole) was charged to the reactor. The mixture was heated to 75° C.

TABLE 2-continued

| Example | C. 7-1 | C. 7-2 | C. 7-3 |
| --- | --- | --- | --- |
| Selectivity to (HQ + CT) (%) | 71.6 | 73.0 | 71.1 |
| CT/HQ (mole/mole) | 1.42 | 1.43 | 1.49 |

Example 6 and Comparative Example 7-1 uses the similar amounts of phenol, hydrogen peroxide, perchloric acid, and pyrophophoric acid, with the exception that the 30 wt. % hydrogen peroxide solution was gradually added to the reaction mixture and water is removed from the reactor during the reaction in Example 6. Example 6 gives >99.8% hydrogen peroxide conversion in the reactor in 60 min, while Comparative Example 7-1 gives only 48.1% hydrogen peroxide conversion in 70 min.

Example 6 gives 86.5% total selectivity to hydroquinone and pyrocatechol relative to $H_2O_2$ converted. In comparison, Comparative Example 7-1 gives 71.6% total selectivity to hydroquinone and pyrocatechol relative to $H_2O_2$ converted.

Example 6 gives a CT/HQ molar ratio of 1.28/1. In comparison, Comparative Example 7-1 gives a CT/HQ molar ratio of 1.42/1.

EXAMPLES 8-9

The apparatus in Example 1 was used. The procedure of Example 1 was followed. Benzophenone was added to the reaction mixture along with phenol, perchloric acid or sulfuric acid, and pyrophosphoric acid. The amounts of reagents used and process conditions are shown in Table 3.

TABLE 3

| Example | 8 | 9 |
|---|---|---|
| Feed | | |
| Phenol (g) | 148.58 | 153.36 |
| 30% $H_2O_2$ (g) | 9.65 | 9.87 |
| 70% $HClO_4$ (g) | 0.14 (0.0010 mol) | |
| 98% $H_2SO_4$ (g) | | 0.10 (0.0010 mol) |
| Benzophenone (g) | 9.97 | 9.94 |
| 90% $H_4P_2O_7$ (g) | 0.14 | 0.14 |
| Pressure (mmHg) | 27 | 27 |
| Bath Temp. (° C.) | 75 | 75 |
| Reactor Temp. during $H_2O_2$ Addition (° C.) | 72 | 72 |
| $H_2O_2$ Addition Time (min) | 44 | 45 |
| Reactor Temp. After $H_2O_2$ Addition (° C.) | 75 | 75 |
| Time After $H_2O_2$ Addition (min) | 6 | 5 |
| Distilled Mixture Collected | | |
| Phenol (g) | 7.70 | 7.94 |
| Pure $H_2O_2$ (g) | 0.050 | 0.41 |
| Reactor Content Wt. (g) | 152.16 | 156.38 |
| Pure $H_2O_2$ (g) | <0.01 | <0.01 |
| Hydroquinone (g) | 4.01 | 3.58 |
| Pyrocatechol (g) | 3.91 | 3.54 |
| Converted $H_2O_2$ (g) | 2.84 | 2.55 |
| (Converted $H_2O_2$)/(Phenol in Feed) (mol/mol) | 0.053 | 0.046 |
| $H_2O_2$ Conversion in Reactor (%) | >99.8 | >99.8 |
| Selectivity to HQ (%) | 43.5 | 43.3 |
| Selectivity to CT (%) | 42.4 | 42.8 |
| Selectivity to (HQ + CT) (%) | 86.0 | 86.2 |
| CT/HQ (mole/mole) | 0.98 | 0.99 |

EXAMPLE 10

The apparatus in Example 1 was used, except that the distillation column was not used. Thus, the distillation head is fitted to the flask directly. The apparatus thus has a single-stage distillation.

The procedure of Example 1 was followed. Benzophenone was added to the reaction mixture along with phenol, perchloric acid, and pyrophosphoric acid. The amounts of reagents used and process conditions are shown in Table 4.

TABLE 4

| Example | 10 |
|---|---|
| Feed | |
| Phenol (g) | 153.57 |
| 30% $H_2O_2$ (g) | 11.52 |
| 70% $HClO_4$ (g) | 0.28 |
| Benzophenone (g) | 10.01 |
| 90% $H_4P_2O_7$ (g) | 0.14 |
| Pressure (mmHg) | 27 |
| Bath Temp. (° C.) | 75 |
| Reactor Temp. during $H_2O_2$ Addition (° C.) | 72 |
| $H_2O_2$ Addition Time (min) | 53 |
| Reactor Temp. After $H_2O_2$ Addition (° C.) | 75 |
| Time After $H_2O_2$ Addition (min) | 7 |
| Distilled Mixture Collected | |
| Phenol (g) | 9.04 |
| Pure $H_2O_2$ (g) | 0.01 |
| Reactor Content Wt. (g) | 156.92 |
| Pure $H_2O_2$ (g) | <0.01 |
| Hydroquinone (g) | 4.86 |
| Pyrocatechol (g) | 4.63 |
| Converted $H_2O_2$ (g) | 3.45 |
| (Converted $H_2O_2$)/(Phenol in Feed) (mol/mol) | 0.062 |
| $H_2O_2$ Conversion in Reactor (%) | >99.8 |
| Selectivity to HQ (%) | 43.5 |
| Selectivity to CT (%) | 41.5 |
| Selectivity to (HQ + CT) (%) | 85.0 |
| CT/HQ (mole/mole) | 0.95 |

EXAMPLES 11-12

The apparatus in Example 1 was used. The procedure of Example 1 was followed. Methyl isobutyl ketone (MIBK) was added to the reaction mixture along with phenol, sulfuric acid, and pyrophosphoric acid at the beginning of the process. The amounts of reagents used and process conditions are shown in Table 5.

TABLE 5

| Example | 11 | 12 |
|---|---|---|
| Feed | | |
| Phenol (g) | 153.49 | 153.85 |
| 30% $H_2O_2$ (g) | 9.84 | 9.70 |
| 98% $H_2SO_4$ (g) | 0.010 | 0.010 |
| MIBK (g) | 9.32 | 4.43 |
| 90% $H_4P_2O_7$ (g) | 0.14 | 0.14 |
| Pressure (mmHg) | 27 | 27 |
| Bath Temp. (° C.) | 75 | 75 |
| Reactor Temp. during $H_2O_2$ Addition (° C.) | 72 | 72 |
| $H_2O_2$ Addition Time (min) | 45 | 43 |
| Reactor Temp. After $H_2O_2$ Addition (° C.) | 75 | 75 |
| Time After $H_2O_2$ Addition (min) | 5 | 7 |
| Distilled Mixture Collected | | |
| Phenol (g) | 7.73 | 7.48 |
| Pure $H_2O_2$ (g) | 0.010 | 0.010 |
| MIBK (g) | 3.46 | 1.50 |
| Reactor Content Wt. (g) | 152.16 | 150.32 |
| Pure $H_2O_2$ (g) | <0.01 | <0.01 |
| Hydroquinone (g) | 3.94 | 3.84 |
| Pyrocatechol (g) | 4.64 | 4.58 |
| Converted $H_2O_2$ (g) | 2.94 | 2.90 |
| (Converted $H_2O_2$)/(Phenol in Feed) (mol/mol) | 0.053 | 0.052 |
| $H_2O_2$ Conversion in Reactor (%) | >99.8 | >99.8 |
| Selectivity to HQ (%) | 41.35 | 40.89 |
| Selectivity to CT (%) | 48.70 | 48.77 |
| Selectivity to (HQ + CT) (%) | 90.05 | 89.65 |
| CT/HQ (mole/mole) | 1.18 | 1.19 |

COMPARATIVE EXAMPLES 13-16

The apparatus in Comparative Example 7 was used. The procedure of Comparative Example 7 was followed. MIBK was added to the reaction mixture along with phenol, sulfuric acid, and pyrophosphoric acid. The amounts of reagents used and detailed process conditions are shown in Table 6.

TABLE 6

| Example | C. 13 | C. 14 | C. 15 |
|---|---|---|---|
| Feed | | | |
| Phenol (g) | 153.23 | 153.2 | 153.51 |
| 30% $H_2O_2$ (g) | 9.72 | 9.6 | 9.54 |
| 98% $H_2SO_4$ (g) | | 0.11 | 0.010 |
| MIBK (g) | 9.08 | 9.11 | 9.18 |
| 90% $H_4P_2O_7$ (g) | 0.14 | 0.14 | 0.14 |
| Reaction Temp. (° C.) | 99 | 75 | 75 |
| Reaction Time (min) | 60 | 60 | 60 |
| $H_2O_2$ Conversion (%) | 74.1 | >99.8 | 93.5 |
| Selectivity to HQ (%) | 25.4 | 33.4 | 30.8 |
| Selectivity to CT (%) | 34.9 | 47.7 | 40.3 |
| Selectivity to (HQ + CT) (%) | 60.3 | 81.1 | 71.1 |
| CT/HQ (mole/mole) | 1.37 | 1.43 | 1.31 |

EXAMPLES 16-18

The apparatus in Example 1 was used. The procedure of Example 1 was followed. Acetophenone was added to the reaction mixture along with phenol, sulfuric acid or sodium bisulfate if used, and pyrophosphoric acid at the beginning of the process. The amounts of reagents used and process conditions are shown in Table 7.

TABLE 7

| Example | 16 | 17 | 18 |
|---|---|---|---|
| Feed | | | |
| Phenol (g) | 153.29 | 153.76 | 153.8 |
| 30% $H_2O_2$ (g) | 9.82 | 9.66 | 9.62 |
| 98% $H_2SO_4$ (g) | | 0.010 | |
| $NaHSO_4 \cdot H_2O$ (g) | | | 0.013 |
| Acetophenone (g) | 11.00 | 11.05 | 11.1 |
| 90% $H_4P_2O_7$ (g) | 0.14 | 0.14 | 0.14 |
| Pressure (mmHg) | 49 | 27 | 27 |
| Bath Temp. (° C.) | 95 | 75 | 75 |
| Reactor Temp. during $H_2O_2$ Addition (° C.) | 92 | 72 | 72 |
| $H_2O_2$ Addition Time (min) | 43 | 43 | 43 |
| Reactor Temp. After $H_2O_2$ Addition (° C.) | 95 | 75 | 75 |
| Time After $H_2O_2$ Addition (min) | 7 | 7 | 7 |
| Distilled Mixture Collected | | | |
| Phenol (g) | 9.80 | 7.78 | 7.69 |
| Pure $H_2O_2$ (9) | 0.16 | 0.036 | 0.12 |
| Reactor Content Wt. (g) | 157.30 | 158.05 | 158.28 |
| Pure $H_2O_2$ (g) | <0.01 | <0.01 | <0.01 |
| Hydroquinone (g) | 3.30 | 4.00 | 4.04 |
| Pyrocatechol (g) | 3.80 | 4.58 | 4.36 |
| Converted $H_2O_2$ (g) | 2.79 | 2.86 | 2.766 |
| (Converted $H_2O_2$)/(Phenol in Feed) (mol/mol) | 0.050 | 0.052 | 0.050 |
| $H_2O_2$ Conversion in Reactor (%) | >99.8 | >99.8 | >99.8 |
| Selectivity to HQ (%) | 36.6 | 43.2 | 45.1 |
| Selectivity to CT (%) | 42.1 | 49.4 | 48.7 |
| Selectivity to (HQ + CT) (%) | 78.7 | 92.6 | 93.8 |
| CT/HQ (mole/mole) | 1.15 | 1.15 | 1.08 |

COMPARATIVE EXAMPLES 19-21

The apparatus in Comparative Example 7 was used. The procedure of Comparative Example 7 was followed. Acetophenone was added to the reaction mixture along with phenol, sulfuric acid or sodium bisulfate if used, and pyrophosphoric acid. The amounts of reagents used and detailed process conditions are shown in Table 8.

TABLE 8

| Example | C. 19 | C. 20 | C. 21 |
|---|---|---|---|
| Feed | | | |
| Phenol (g) | 153.39 | 153.78 | 153.44 |
| 30% $H_2O_2$ (g) | 9.78 | 9.81 | 9.73 |
| 98% $H_2SO_4$ (g) | | 0.010 | |
| $NaHSO_4 \cdot H_2O$ (g) | | | 0.013 |
| Acetophenone (g) | 11.02 | 11.26 | 11.04 |
| 90% $H_4P_2O_7$ (g) | 0.14 | 0.14 | 0.14 |
| Reaction Temp. (° C.) | 95 | 75 | 75 |
| Reaction Time (min) | 60 | 60 | 60 |
| $H_2O_2$ Conversion (%) | 63.4 | 81.7 | 56.9 |
| Selectivity to HQ (%) | 30.3 | 37.4 | 37.1 |
| Selectivity to CT (%) | 40.6 | 44.8 | 49.1 |
| Selectivity to (HQ + CT) (%) | 70.9 | 82.2 | 86.2 |
| CT/HQ (mole/mole) | 1.34 | 1.20 | 1.32 |

EXAMPLE 22

The apparatus in Example 1 was used. The procedure of Example 1 was followed. 2-Octanone was added to the reaction mixture along with phenol, sodium bisulfate, and pyrophosphoric acid at the beginning of the process. The amounts of reagents used and process conditions are shown in Table 9.

TABLE 9

| Example | 22 |
|---|---|
| Feed | |
| Phenol (g) | 153.8 |
| 30% $H_2O_2$ (g) | 9.80 |
| $NaHSO_4 \cdot H_2O$ (g) | 0.014 |
| 2-Octanone (g) | 11.00 |
| 90% $H_4P_2O_7$ (g) | 0.14 |
| Pressure (mmHg) | 27 |
| Bath Temp. (° C.) | 75 |
| Reactor Temp. during $H_2O_2$ Addition (° C.) | 72 |
| $H_2O_2$ Addition Time (min) | 43 |
| Reactor Temp. After $H_2O_2$ Addition (° C.) | 75 |
| Time After $H_2O_2$ Addition (min) | 7 |
| Distilled Mixture Collected | |
| Phenol (g) | 7.62 |
| Pure $H_2O_2$ (g) | 0.048 |
| Reactor Content Wt. (g) | 158.37 |
| Pure $H_2O_2$ (g) | <0.01 |
| Hydroquinone (g) | 3.91 |
| Pyrocatechol (g) | 4.46 |
| Converted $H_2O_2$ (g) | 2.89 |
| (Converted $H_2O_2$)/(Phenol in Feed) (mol/mol) | 0.052 |
| $H_2O_2$ Conversion in Reactor (%) | >99.8 |
| Selectivity to HQ (%) | 41.7 |
| Selectivity to CT (%) | 47.6 |
| Selectivity to (HQ + CT) (%) | 89.4 |
| CT/HQ (mole/mole) | 1.14 |

COMPARATIVE EXAMPLE 23

The apparatus in Comparative Example 7 was used. The procedure of Comparative Example 7 was followed. 2-Octanone was added to the reaction mixture along with phenol, sodium bisulfate, and pyrophosphoric acid. The amounts of reagents used and detailed process conditions are shown in Table 10.

TABLE 10

| Example | C. 23 |
|---|---|
| Feed | |
| Phenol (g) | 153.94 |
| 30% $H_2O_2$ (g) | 9.89 |
| 98% $H_2SO_4$ | (g) |
| $NaHSO_4 \cdot H_2O$ (g) | 0.013 |
| 2-Octanone (g) | 10.95 |
| 90% $H_4P_2O_7$ (g) | 0.14 |
| Reaction Temp. (° C.) | 75 |
| Reaction Time (min) | 60 |
| $H_2O_2$ Conversion (%) | 70.1 |
| Selectivity to HQ (%) | 25.0 |
| Selectivity to CT (%) | 35.8 |
| Selectivity to (HQ + CT) (%) | 60.8 |
| CT/HQ (mole/mole) | 1.43 |

I claim:

1. A process for hydroxylating a phenolic substrate, comprising: reacting the phenolic substrate and hydrogen peroxide in the presence of a catalyst selected from the group consisting of a strong acid, a ketone, and mixtures thereof, in a reaction mixture; and simultaneously removing water from the reaction mixture.

2. The process of claim 1, wherein water is removed from the reaction mixture by distillation.

3. The process of claim 2, wherein the distillation is performed with a distillation column.

4. The process of claim 3, wherein the distillation column has from 2 to 30 theoretical plates.

5. The process of claim 2, wherein the distillation is performed under sub-atmospheric pressure.

6. The process of claim 1, wherein the reaction mixture has a water content of less than 1.0 wt. %.

7. The process of claim 1, wherein the reaction mixture has a water content of less than 0.50 wt. %.

8. The process of claim 1, wherein the strong acid has a pKa in water of less than −0.1.

9. The process of claim 1, wherein the strong acid has a pKa in water of less than −5.0.

10. The process of claim 1, wherein the catalyst is a ketone.

11. The process of claim 10, performed in the presence of a sulfur-containing promoter.

12. The process of claim 1, performed at a temperature of from 30 to 180° C.

13. The process of claim 1, wherein the phenolic substrate is phenol.

14. The process of claim 1, performed in the presence of a complexing agent.

15. The process of claim 14, wherein the complexing agent is pyrophosphoric acid.

* * * * *